(12) United States Patent
Hong et al.

(10) Patent No.: US 12,201,426 B2
(45) Date of Patent: Jan. 21, 2025

(54) ELECTRONIC DEVICE AND METHOD FOR PROVIDING PERSONALIZED BIOMETRIC INFORMATION BASED ON BIOMETRIC SIGNAL USING SAME

(71) Applicant: Samsung Electronics Co., Ltd., Suwon-si (KR)

(72) Inventors: Hyunsu Hong, Suwon-si (KR); Sangbeom Nam, Suwon-si (KR); Yongjin Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 18/630,466

(22) Filed: Apr. 9, 2024

(65) Prior Publication Data

US 2024/0252086 A1 Aug. 1, 2024

Related U.S. Application Data

(63) Continuation of application No. 18/181,168, filed on Mar. 9, 2023, which is a continuation of application
(Continued)

(30) Foreign Application Priority Data

Jul. 2, 2018 (KR) .................. 10-2018-0076439

(51) Int. Cl.
*A61B 5/11* (2006.01)
*A61B 5/00* (2006.01)
(Continued)

(52) U.S. Cl.
CPC ............ *A61B 5/165* (2013.01); *A61B 5/0002* (2013.01); *A61B 5/1118* (2013.01);
(Continued)

(58) Field of Classification Search
CPC ...... A61B 5/165; A61B 5/0002; A61B 5/1118; A61B 5/7235; A61B 5/7405; A61B 5/7425; A61B 2562/0219; G08B 21/18
(Continued)

(56) References Cited

U.S. PATENT DOCUMENTS 6,095,984 A 8/2000 Amano et al.
6,128,526 A 10/2000 Stadler et al.
(Continued)

FOREIGN PATENT DOCUMENTS

CN 1909828 A 2/2007
CN 105930631 A 9/2016
(Continued)

OTHER PUBLICATIONS

International Search Report and Written Opinion dated Aug. 29, 2019, issued in an International application No. PCT/KR2019/006158.
(Continued)

*Primary Examiner* — Hirdepal Singh
(74) *Attorney, Agent, or Firm* — Jefferson IP Law, LLP

(57) ABSTRACT

An electronic device for providing biometric information is provided. The electronic device includes a sensor module, a memory, and a processor electrically connected to the sensor module and the memory. The processor obtains a biometric signal from the sensor module at a predetermined time interval, determines whether a user is in a first state on the basis of the obtained biometric signal, in case the user is in a first state, obtains a representative value for a respective of the at least one biometric signal, defines the obtained representative value for the respective of the at least one biometric signal as a candidate reference value for a corresponding biometric signal, determines a candidate reference value satisfying a predetermined condition as a first refer-
(Continued)

ence value for the corresponding biometric signal, and updates a second reference value previously configured for the corresponding biometric signal on the basis of the first reference value.

18 Claims, 6 Drawing Sheets

Related U.S. Application Data

No. 17/069,333, filed on Oct. 13, 2020, now Pat. No. 11,602,295, which is a continuation of application No. 16/419,678, filed on May 22, 2019, now Pat. No. 10,806,389.

(51) Int. Cl.
*A61B 5/16* (2006.01)
*G08B 21/18* (2006.01)

(52) U.S. Cl.
CPC .......... *A61B 5/7235* (2013.01); *A61B 5/7405* (2013.01); *A61B 5/7425* (2013.01); *G08B 21/18* (2013.01); *A61B 2562/0219* (2013.01)

(58) Field of Classification Search
USPC ...................................... 340/573.1
See application file for complete search history.

(56) References Cited

U.S. PATENT DOCUMENTS

| | | | |
|---|---|---|---|
| 8,594,776 B2 | 11/2013 | McCombie et al. | |
| 8,734,296 B1 | 5/2014 | Brumback et al. | |
| 9,510,790 B2 | 12/2016 | Kang et al. | |
| 9,852,599 B1 | 12/2017 | Slavin et al. | |
| 10,013,870 B2 | 7/2018 | Treccani | |
| 11,838,990 B2 * | 12/2023 | Virkkala | H04L 67/12 |
| 2007/0167850 A1 | 7/2007 | Russell et al. | |
| 2007/0208532 A1 | 9/2007 | Park et al. | |
| 2010/0160761 A1 | 6/2010 | Say et al. | |
| 2013/0278414 A1 | 10/2013 | Sprigg et al. | |
| 2014/0206946 A1 | 7/2014 | Kim et al. | |
| 2015/0150516 A1 | 6/2015 | Tochikubo et al. | |
| 2016/0232317 A1 | 8/2016 | Kim et al. | |
| 2016/0287142 A1 | 10/2016 | Han et al. | |
| 2016/0367138 A1 | 12/2016 | Kim et al. | |
| 2017/0035365 A1 | 2/2017 | Hasegawa et al. | |
| 2017/0042485 A1 | 2/2017 | Chung et al. | |
| 2017/0224273 A1 * | 8/2017 | Vardas | A61B 5/486 |
| 2017/0296088 A1 | 10/2017 | Choi | |
| 2018/0114081 A1 | 4/2018 | Dejewski et al. | |
| 2018/0206725 A1 | 7/2018 | Everett et al. | |
| 2018/0225417 A1 | 8/2018 | Bostick et al. | |
| 2019/0209027 A1 | 7/2019 | Miyashita et al. | |
| 2019/0370448 A1 * | 12/2019 | Devine | G06V 40/67 |
| 2021/0100483 A1 | 4/2021 | Foxlin et al. | |
| 2021/0393210 A1 | 12/2021 | LeBoeuf et al. | |

FOREIGN PATENT DOCUMENTS

| | | |
|---|---|---|
| CN | 106055084 A | 10/2016 |
| CN | 106415683 A | 2/2017 |
| EP | 2 759 259 A2 | 7/2014 |
| KR | 10-2005-0025554 A | 3/2005 |
| KR | 10-2016-0096455 A | 8/2016 |
| KR | 10-2016-0149911 A | 12/2016 |
| KR | 10-2017-0093470 A | 8/2017 |
| KR | 10-2017-0118439 A | 10/2017 |
| KR | 10-2018-0037157 A | 4/2018 |
| WO | 2015/107891 A1 | 7/2015 |

OTHER PUBLICATIONS

Extended European Search Report dated Jul. 23, 2021, issued in European Patent Application No. 19830443.8.
Korean Office Action dated Jan. 3, 2023, issued in Korean Patent Application No. 10-2018-0076439.
Chinese Office Action dated Jun. 29, 2023, issued in Chinese Application No. 201980044630.X.
Decision to Grant a Patent dated Apr. 18, 2024, issued in Chinese Application No. 201980044630.X.
U.S. Office Action dated Jul. 17, 2024, issued in U.S. Appl. No. 18/181,168.
European Office Action dated Aug. 14, 2024, issued in European Application No. 19 830 443.8-1113.

* cited by examiner

ELECTRONIC DEVICE AND METHOD FOR PROVIDING PERSONALIZED BIOMETRIC INFORMATION BASED ON BIOMETRIC SIGNAL USING SAME

CROSS-REFERENCE TO RELATED APPLICATION(S)

This application is a continuation application of prior application Ser. No. 18/181,168, filed on Mar. 9, 2023, which is a continuation application of prior application Ser. No. 17/069,333, filed on Oct. 13, 2020, which has issued as U.S. Pat. No. 11,602,295 on Mar. 14, 2023; which is a continuation application of prior application Ser. No. 16/419,678, filed on May 22, 2019, which has issued as U.S. Pat. No. 10,806,389 on Oct. 20, 2020, and which claimed the benefit under 35 U.S.C. § 119(a) of a Korean patent application number 10-2018-0076439, filed on Jul. 2, 2018, in the Korean Intellectual Property Office, the disclosure of which is incorporated by reference herein in its entirety.

BACKGROUND

1. Field

Various embodiments of the disclosure relate to an electronic device and a method for providing personalized biometric information based on a biometric signal.

2. Description of Related Art

In general, electronic devices have various kinds of sensors. The electronic devices may monitor user's behavior in real time using various kinds of sensors provided therein. The electronic devices may estimate biometric information (e.g., heart rate information, blood pressure information, stress information, etc.) related to the user on the basis of biometric signals obtained through monitoring of various sensors, and may provide the estimated biometric information to the user.

The above information is presented as background information only to assist with an understanding of the disclosure. No determination has been made, and no assertion is made, as to whether any of the above might be applicable as prior art with regard to the disclosure.

SUMMARY

However, since a generalized model is used for estimating the biometric information related to the user despite the factors causing changes in the body characteristics and biometric signals are different between users, accurate biometric information (e.g., stress intensity) may not be provided to the user.

Aspects of the disclosure are to address at least the above-mentioned problems and/or disadvantages and to provide at least the advantages described below. Accordingly, an aspect of the disclosure is to provide an electronic device that detects changes in the biometric signals (e.g., heart rate, blood pressure, skin temperature, skin resistance, etc.) obtained from sensors, and may store only the biometric signals in the state in which no change is detected. The electronic device may determine personalized biometric information for the user on the basis of the stored biometric signals, and provide the user with information on the biometric state on the basis of the determined biometric information.

Additional aspects will be set forth in part in the description which follows and, in part, will be apparent from the description, or may be learned by practice of the presented embodiments.

In accordance with an aspect of the disclosure, an electronic device is provided. The electronic device includes a sensor module, a memory, and at least one processor electrically connected to the sensor module and the memory, wherein the processor is configured to obtain at least one biometric signal from the sensor module at a predetermined time interval, determine whether a user is in a first state on the basis of the obtained at least one biometric signal, in case the user is in the first state, obtain a representative value for a respective of the at least one biometric signal, define the obtained representative value for the respective of the at least one biometric signal as a candidate reference value for a corresponding biometric signal, determine a candidate reference value satisfying a predetermined condition as a first reference value for the corresponding biometric signal, and update a second reference value previously configured for the corresponding biometric signal on the basis of the first reference value.

In accordance with another aspect of the disclosure, a method of providing personalized biometric information based on a biometric signal is provided. The method includes obtaining at least one biometric signals from a sensor module at a predetermined time interval, determining whether a user is in a first state on the basis of the obtained at least one biometric signal, in case the user is in the first state, obtaining a representative value for a respective of the at least one biometric signal, defining the obtained representative value for the respective of the at least one biometric signal as a candidate reference value for a corresponding biometric signal, determining a candidate reference value satisfying a predetermined condition as a first reference value for the corresponding biometric signal, and updating a second reference value previously configured for the corresponding biometric signal on the basis of the first reference value.

An electronic device according to various embodiments is able to determine a personalized reference value for a biometric signal on the basis of a biometric signal in the state in which no change in the biometric signal obtained from the sensors is detected. The electronic device is able to provide the user with accurate biometric information (e.g., stress intensity) by comparing a personalized reference value for a biometric signal with biometric signal values obtained from the sensors.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, like reference numerals will be understood to refer to like parts, components, and structures.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
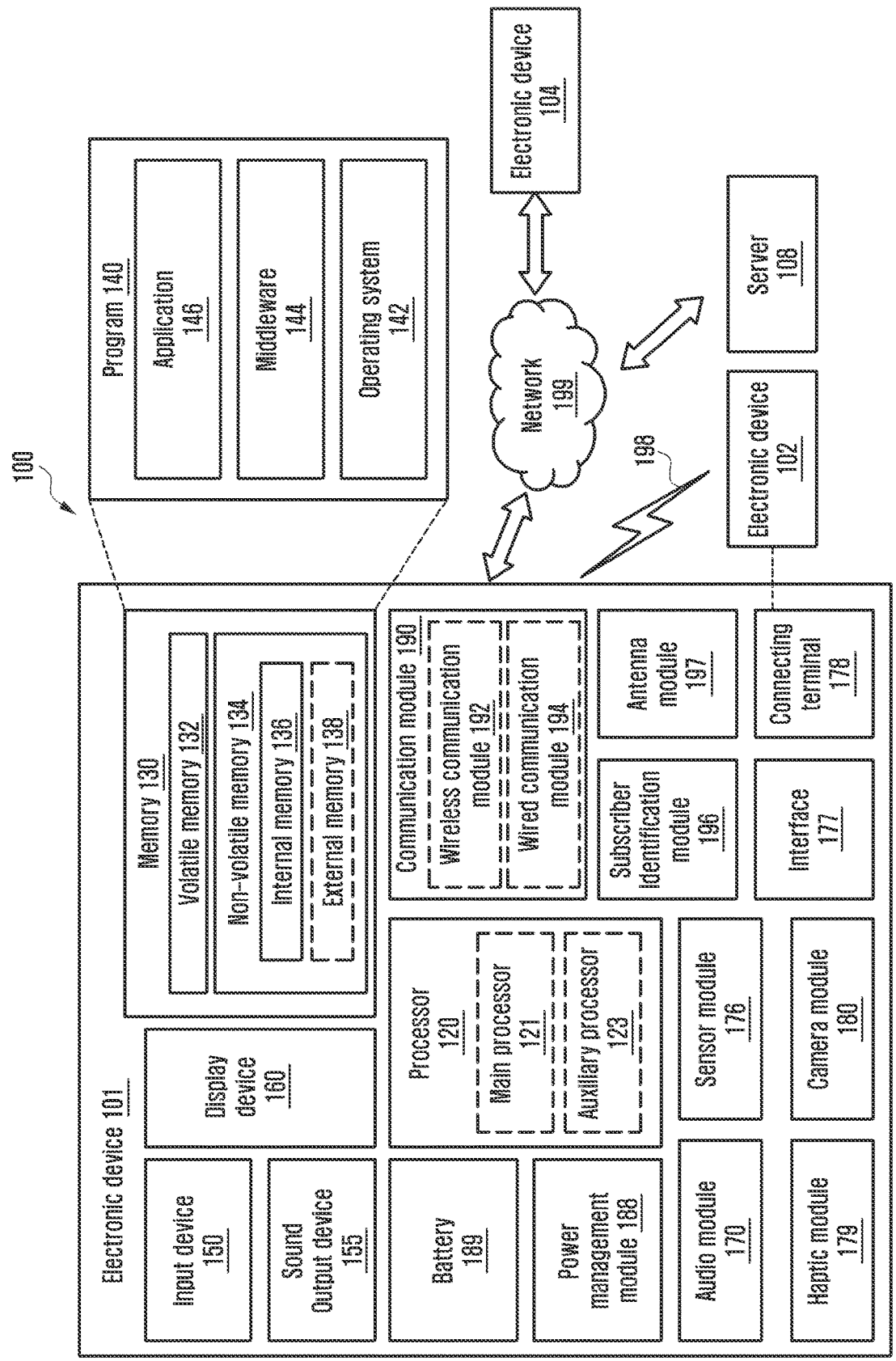
FIG. 1 is a block diagram of an electronic device that provides personalized biometric information based on a biometric signal in a network environment according to various embodiments of the disclosure.

FIG. 1 is a block diagram of an electronic device 101 that provides personalized biometric information based on a biometric signal in a network environment 100 according to various embodiments of the disclosure.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190 (e.g., a transceiver), a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, or a keyboard.

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming call. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, an HDMI connector, a USB connector, an SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) (e.g., a wireless transceiver) or a wired communication module 194 (e.g., a local area network (LAN) communication module or a power line communication (PLC) module) (e.g., a wired transceiver). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., local area network (LAN) or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include one or more antennas, and, therefrom, at least one antenna appropriate for a communication scheme used in the communication network, such as the first network 198 or the second network 199, may be selected, for example, by the communication module 190 (e.g., the wireless communication module 192). The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
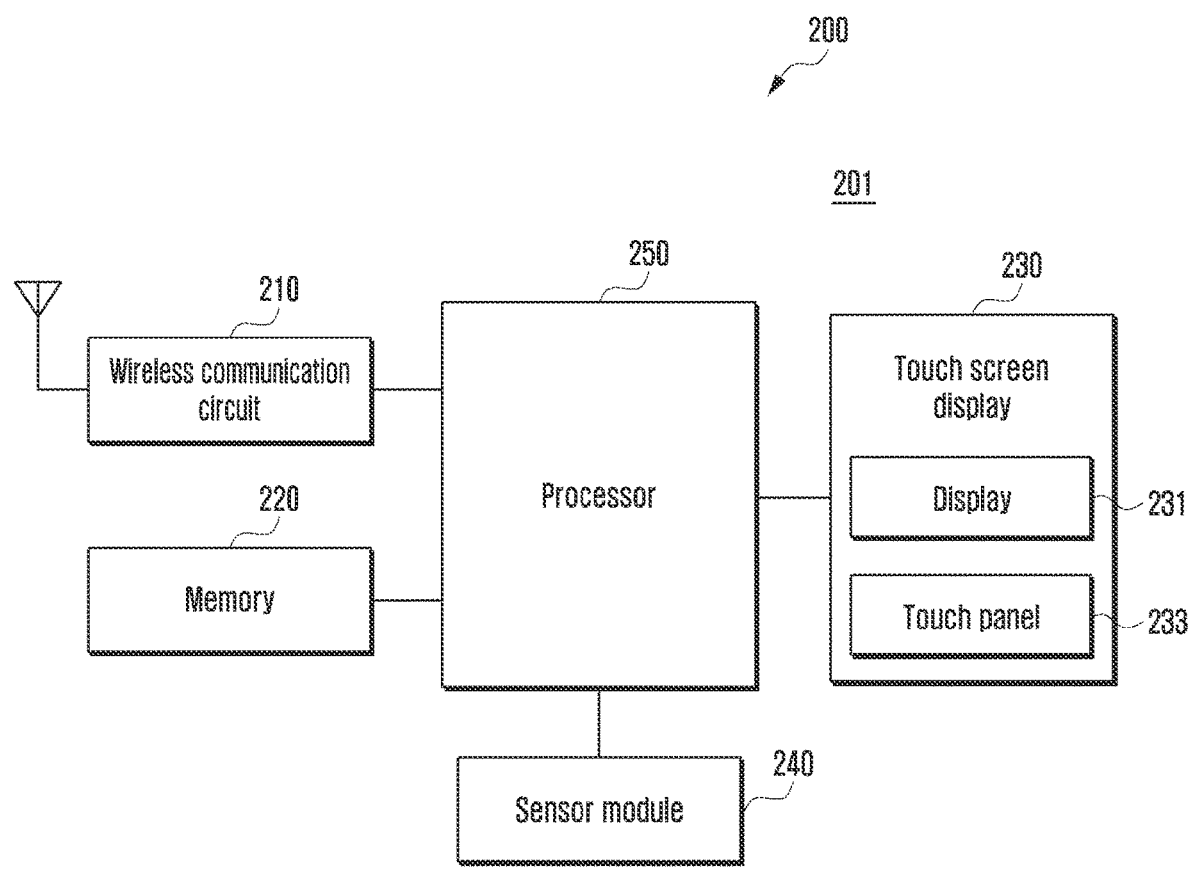
FIG. 2 is a block diagram illustrating an electronic device that provides personalized biometric information based on a biometric signal according to various embodiments of the disclosure.

FIG. 2 is a block diagram 200 illustrating an electronic device that provides personalized biometric information based on a biometric signal according to various embodiments of the disclosure.

Referring to FIG. 2, an electronic device 201 (e.g., the electronic device 101 of FIG. 1) may include a wireless communication circuit 210 (e.g., the wireless communication module 192 in FIG. 1), a memory 220 (e.g., the memory 130 in FIG. 1), a touch screen display 230 (e.g., the display device 160 in FIG. 1), a sensor module 240 (e.g., the sensor module 176 in FIG. 1), and a processor 250 (e.g., the processor 120 in FIG. 1).

In an embodiment, the electronic device 201 may be a wearable device.

In an embodiment, the wireless communication circuit 210 may establish communications between the electronic device 201 and external electronic device (e.g., the electronic devices 102 and 104, the server 108 in FIG. 1).

In an embodiment, the electronic device 201 may transmit biometric information of a user (e.g., biometric signals, biometric states, etc.) obtained through the sensor module 240 to an external electronic device through the wireless communication circuit 210. The external electronic device may store the biometric information of the user received from the electronic device 201.

In an embodiment, the electronic device 201 may receive, from the external electronic device, external information, which is a reference for determining a reference value for the biometric signal, through the wireless communication circuit 210. The external information may include demographic information. For example, the demographic information may include information such as gender, age, climate, race, and the like.

In an embodiment, the memory 220 may store a program for measuring user's biometric signals, a program for determining a personalized reference value on the basis of the user's biometric signals, and a program for determining the biometric state of the user on the basis of the same.

In an embodiment, the memory 220 may store a reference value for determining the activity state of the user. For example, the memory 220 may store reference patterns for the activity state of the user, such as a dynamic state, a static state (e.g., a static stable state or a static unstable state), and a stable state.

In an embodiment, the memory 220 may store biometric information of the user (e.g., biometric signals, biometric states, etc.) obtained through the sensor module 240.

In an embodiment, the touch screen display 230 may be configured as an integral unit including a display 231 and a touch panel 233.

In an embodiment, the touch screen display 230 may display sensor information of the user (e.g., heart rate (HR), blood pressure (BP), and the like), which is obtained from the sensor module 240 under the control of the processor 250. The touch screen display 230 may display information related to the biometric state of the user under the control of the processor 250. For example, the information related to the biometric state of the user may include health information, stress information, blood pressure information, and the like. The touch screen display 230 may output the information related to the biometric state of the user in the form of a message, a pop-up window, or the like under the control of the processor 250. However, the disclosure is not limited thereto, and the information related to the biometric state of the user may be output as a sound through a speaker (e.g., the sound output device 155 in FIG. 1).

In an embodiment, the sensor module 240 may include a biometric sensor (e.g., a photoplethysmography (PPG) sensor or a skin temperature sensor), an acceleration sensor, and the like.

In an embodiment, the sensor module 240 (e.g., the acceleration sensor) may detect the motion of the electronic device 201. The sensor module 240 may transmit a sensor signal according to the motion of the electronic device 201 to the processor 250.

In an embodiment, the sensor module 240 (e.g., the PPG sensor) may obtain a continuous PPG value. For example, the PPG value may include a heart rate, a blood pressure, and the like. The sensor module 240 may transmit the obtained PPG value to the processor 250.

In an embodiment, the processor 250 may control the overall operation of the electronic device 201 and signal flows between internal components of the electronic device 201, may perform data processing, and may control power supply from a battery (e.g., the battery 189 in FIG. 1) to the above components.

In an embodiment, the processor 250 may obtain at least one biometric signal through the sensor module 240 at a predetermined time interval. The processor 250 may determine the activity state of the user (e.g., a dynamic state (e.g., walking or running), a static state (e.g., a static stable state or a static unstable state), and a stable state) on the basis of at least one biometric signal obtained from the sensor module 240.

In an embodiment, the processor 250 may compare a predetermined motion pattern for the activity state of the user, which is stored in the memory 220, with a motion pattern of the electronic device 201, which is measured through the sensor module 240 (e.g., the acceleration sensor). The processor 250 may determine the activity state of the user on the basis of the comparison result. The processor 250 may compare a predetermined sensor value for the activity state of the user, which is stored in the memory 220, with a PPG sensor value obtained through the sensor module 240 (e.g., the PPG sensor or the skin temperature sensor). The processor 250 may determine the activity state of the user on the basis of the comparison result.

In an embodiment, the processor 250 may determine the activity state of the user on the basis of a change in the biometric signal.

In an embodiment, the processor 250 may determine whether or not the user is in the stable state on the basis of at least one of the pattern comparison or a change in the biometric signal. If the user is in the stable state, the processor 250 may obtain a representative value for the respective of the at least one biometric signal. The processor 250 may define the obtained representative value for the respective of the at least one biometric signal as a candidate reference value for a corresponding biometric signal. For example, the representative value for the respective of the at least one biometric signal may include one of a minimum value, a maximum value, an average value, a mode value, a median value, an interval initial value, and a final value for the respective of the at least one biometric signal.

In an embodiment, if the user is determined to be in the stable state, the processor 250 may store, in the memory 220, the respective of the at least one biometric signal (e.g., heart rate, heart rate variation, and blood pressure values) in the interval of the stable state.

In an embodiment, the processor 250 may determine a candidate reference value that satisfies a predetermined condition as a first reference value for the corresponding biometric signal. For example, the predetermined condition may include at least one of whether or not the candidate reference value is included within a specific range of the histogram for each biometric signal in the stable state, which has been obtained recently for a predetermined period of time, or whether or not the candidate reference value is included within a specific range of external information (e.g., demographic information).

In an embodiment, the processor 250 may update a second reference value, which was previously configured for the corresponding biometric signal, on the basis of the first reference value.

In an embodiment, the processor 250 may compare a value of at least one biometric signal obtained from the sensor module 240 with a reference value corresponding to the at least one biometric signal. The processor 250 may provide a notification of personalized information related to the biometric state of the user determined on the basis of the comparison result. The personalized information related to the biometric state of the user may include health information, stress information, blood pressure information, and the like. The processor 250 may provide the personalized information related to the biometric state of the user in the form of at least one of a message, a pop-up window, or a sound.

Figure 3:
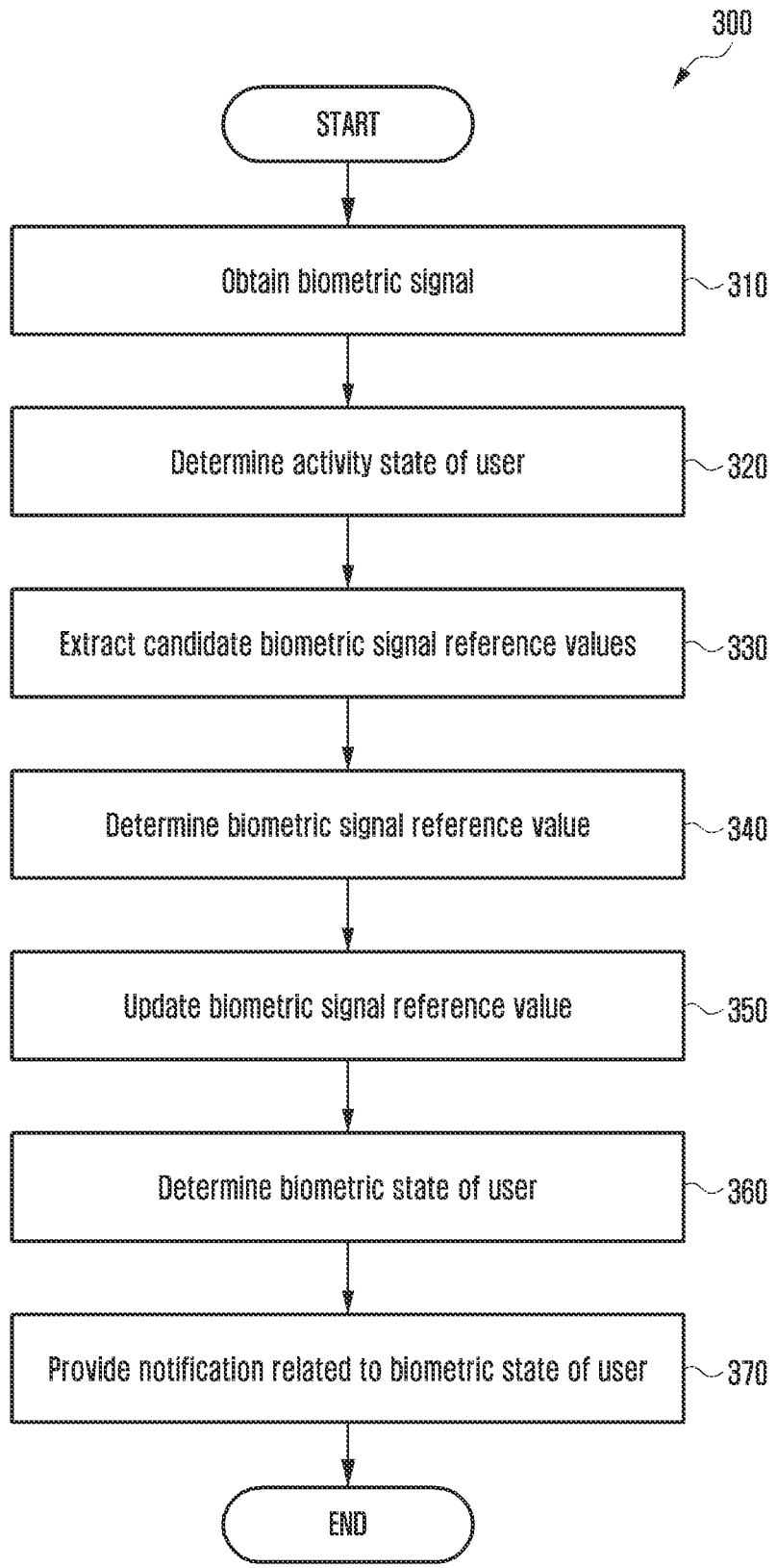
FIG. 3 is a flowchart explaining a method for providing personalized biometric information based on a biometric signal according to various embodiments of the disclosure.

FIG. 3 is a flowchart 300 explaining a method for providing personalized biometric information based on a biometric signal according to various embodiments of the disclosure.

Referring to FIG. 3, the processor (e.g., the processor 250 in FIG. 2) may obtain biometric signals in operation 310. For example, the processor may obtain at least one biometric signal from the sensor module (e.g., the sensor module 240 in FIG. 2). For example, the at least one biometric signal may include a continuous PPG value obtained from a sensor module, such as a PPG sensor, a continuous skin temperature value obtained from a skin temperature sensor, and a continuous acceleration value for the motion of the electronic device (e.g., the electronic device 201 in FIG. 2) obtained from an acceleration sensor.

In an embodiment, the processor may determine the activity state of a user in operation 320. The processor may determine the activity state of the user on the basis of at least one biometric signal obtained from the sensor module. For example, the activity state of the user may include a dynamic state, a static state (e.g., a static stable state or a static unstable state), and a stable state.

In an embodiment, a reference pattern for the activity state of the user, such as a dynamic state, a static state (e.g., a static stable state or a static unstable state), or a stable state, may be pre-stored in the memory (e.g., the memory 220 in FIG. 2).

In an embodiment, the processor may determine the activity state of the user by comparing the reference pattern of the activity state of the user, which was pre-stored in memory, with at least one biometric signal obtained from the sensor module.

In an embodiment, the processor may extract candidate reference values for the biometric signals in operation 330. In operation 330 described above, if the activity state of the user is determined to be a stable state, the processor may extract representative values for the respective biometric signal values in the interval during which the activity state of the user is determined to be a stable state. The processor may define the extracted representative values for the respective biometric signal values as candidate reference value for the corresponding biometric signal.

In an embodiment, the processor may determine a reference value for the biometric signal in operation 340. The processor may determine a candidate reference value that satisfies a predetermined condition, among the defined candidate reference values for the corresponding biometric signal, as a reference value for the corresponding biometric signal. For example, the predetermined condition may include at least one of a histogram or external information (e.g., demographic information).

In an embodiment, the processor may determine a candidate reference value satisfying at least one of a specific range of the histogram or the external information, among the candidate reference values for the corresponding biometric signal, as a reference value for the corresponding biometric signal.

In an embodiment, the processor may update a reference value for the biometric signal in operation 350. The processor may update a reference value, which was previously configured for the corresponding biometric signal, on the basis of the reference value determined in operation 340.

In an embodiment, the processor may determine the biometric state of the user in operation 360. The processor may compare the reference value for the biometric signal, which is updated in operation 350, with at least one biometric signal obtained from the sensor module, thereby determining the biometric state of the user on the basis of the same.

In an embodiment, the processor may provide a notification related to the biometric state of the user in operation 370. The processor may provide a notification of information related to the biometric state of the user on the basis of the biometric state of the user determined in operation 360. For example, the information related to the biometric state of the user may include a user's stress level and the like.

In an embodiment, the above-described operations in FIG. 3 will be described in detail with reference to FIGS. 4 to 6.

Figure 4:
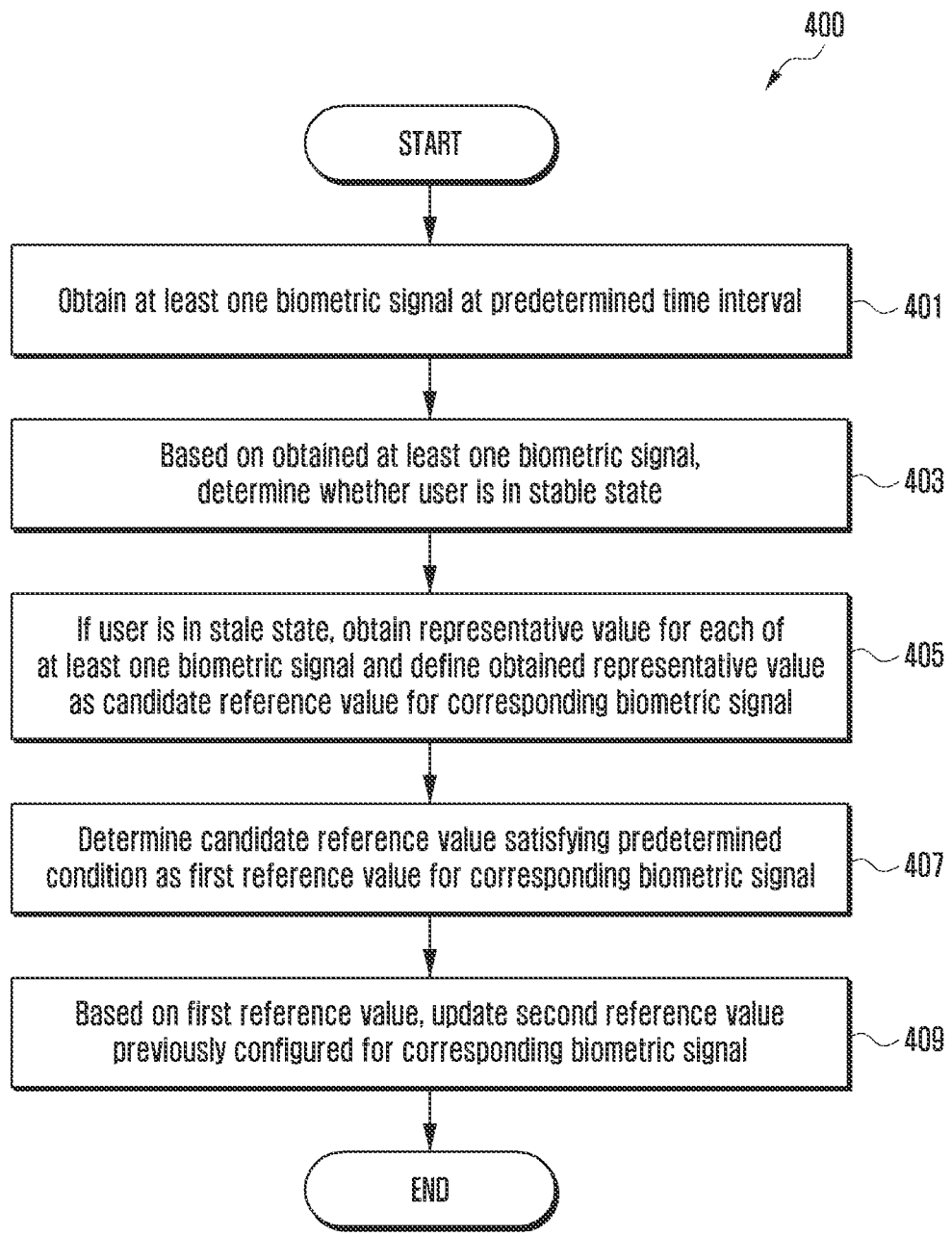
FIG. 4 is a flowchart explaining a method for determining a reference value for providing personalized biometric information based on a biometric signal according to various embodiments of the disclosure.

FIG. 4 is a flowchart 400 explaining a method for determining a reference value for providing personalized biometric information based on a biometric signal according to various embodiments of the disclosure.

Referring to FIG. 4, a processor (e.g., the processor 250 in FIG. 2) may obtain at least one biometric signal through a sensor module (e.g., the sensor module 240 in FIG. 2) at a predetermined time interval in operation 401.

In an embodiment, the processor may monitor the sensor module provided in the electronic device (e.g., the electronic device 201 in FIG. 2), thereby obtaining at least one biometric signal. For example, the sensor module may include a biometric sensor (e.g., a PPG sensor or a skin temperature sensor), an acceleration sensor, and the like.

In an embodiment, the processor may obtain a continuous PPG value, such as a heart rate value, a blood pressure value, or the like, from the biometric sensor (e.g., the PPG sensor). The processor may obtain a continuous skin temperature value from the biometric sensor (e.g., the skin temperature sensor). The processor may obtain a continuous acceleration value for the motion of the electronic device through the acceleration sensor.

In an embodiment, the processor may determine whether or not the user is in the stable state on the basis of at least one biometric signal obtained from the sensor module in operation 403.

In an embodiment, the processor may analyze a motion pattern of the electronic device using an acceleration value measured through the acceleration sensor. The processor may determine the activity state of the user (e.g., a dynamic state (e.g., walking or running) or a static state (e.g., a static stable state or a static unstable state)) on the basis of the motion pattern of the electronic device.

In an embodiment, the motion pattern for the activity state of the user may be predefined, and may be stored in the memory (e.g., the memory 220 in FIG. 2).

In an embodiment, the processor may compare the predefined motion pattern stored in the memory with the motion pattern of the electronic device, which is measured through the acceleration sensor, thereby determining the activity state of the user on the basis of the same.

In an embodiment, if a user's motion is detected through the acceleration sensor, the processor may determine that the electronic device is in a dynamic state. For example, the dynamic state may include an exercise state of the user (e.g., walking or running).

In an embodiment, the processor may obtain a biometric signal through a biometric sensor.

In an embodiment, if the user is in the exercise state, the obtained biometric signal may vary. For example, if the user is in the exercise state, the user's heart rate or skin temperature may increase.

In an embodiment, if no motion of the electronic device is detected through the acceleration sensor, and if the changed state of the biometric signal is maintained for a predetermined period of time, the processor may determine that the user is in a static stable state.

In an embodiment, the example in which no motion of the electronic device is detected may include the case where the user has finished the exercise, such as walking, running, and the like.

In an embodiment, if no motion of the electronic device is detected, but if the heart rate is increased, or if the increased heart rate is maintained for a predetermined period of time due to an oxygen debt immediately after exercise, the processor may determine that the user is in a static unstable state.

In an embodiment, if no motion of the electronic device is detected through the acceleration sensor, and if the biometric signal obtained through the biometric sensor is increased, compared to a predefined biometric signal, the processor may determine that the user is in a static unstable state. For example, the static unstable state may include the states in which the heart rate and the blood pressure are increased and the skin temperature is reduced due to emotional awakening and stress, in which the heart rate is increased and the blood pressure is reduced due to drinking, and in which the heart rate and the blood pressure are increased due to smoking.

In an embodiment, if the user is not in the dynamic state and the static state (e.g., the static stable state or the static unstable state), the processor may determine that the user is in the stable state. For example, if a user's motion and a biometric signal (e.g., a change in the heart rate and the blood pressure) are not detected for a predetermined period of time, the processor may determine that the user is in the stable state.

In an embodiment, if the user is in the stable state, the processor may obtain representative value for each at least one biometric signal, and may define the obtained representative value as candidate reference value for the corresponding biometric signal in operation 405.

In an embodiment, if the stable state of the user is maintained for a predetermined period of time, the processor may obtain representative value for respective biometric signals in the interval during which the user is determined to be in the stable state. The processor may determine the obtained representative values for the respective biometric signals as candidate reference values for the one or more biometric signals.

In an embodiment, the representative values for the respective biometric signals in the interval during which the user is determined to be in the stable state may include one of a minimum value, a maximum value, an average value, a mode value, a median value, an interval initial value, and a final value for the respective biometric signals.

In an embodiment, if the user is determined to be in the stable state, the processor may store, in the memory, respective biometric signal values, such as a heart rate value, a heart rate variation, and a blood pressure value, in the stable-state interval.

In an embodiment, the processor may determine a candidate reference value that satisfies a predetermined condition as a first reference value for the corresponding biometric signal in operation 407.

In an embodiment, the predetermined condition may include at least one of whether or not the candidate reference value is included within a specific range of a histogram for each biometric signal in the stable state, which has recently been obtained for a predetermined period of time, or whether or not the candidate reference value is included within a specific range of demographic information.

In an embodiment, the processor may configure a specific range on the histogram that records each biometric signal in the stable state, and may determine whether or not the candidate reference value of each biometric signal is included within a reference range on the histogram that records each biometric signal.

In an embodiment, if the candidate reference value of each biometric signal is included within a specific range on the histogram for each biometric signal, the processor may determine the candidate reference value to be a first reference value for the corresponding biometric signal.

In an embodiment, the rage of the reference value based on the demographic information may include a reference range that can be obtained on the basis of references, such as age, gender, and the like.

In an embodiment, if the candidate reference value of each biometric signal is included within the range of the reference value based on the demographic information, the processor may determine the biometric signal reference value included in the range of the reference value based on demographic information as the first reference value.

In an embodiment, the processor may update a second reference value, which was previously configured for the corresponding biometric signal, on the basis of the first reference value in operation 409.

In an embodiment, the updated reference value may be used as a reference value for determining the biometric state of the user (e.g., a stress level) on the basis of each of obtained at least one biometric signal.

Figure 5:
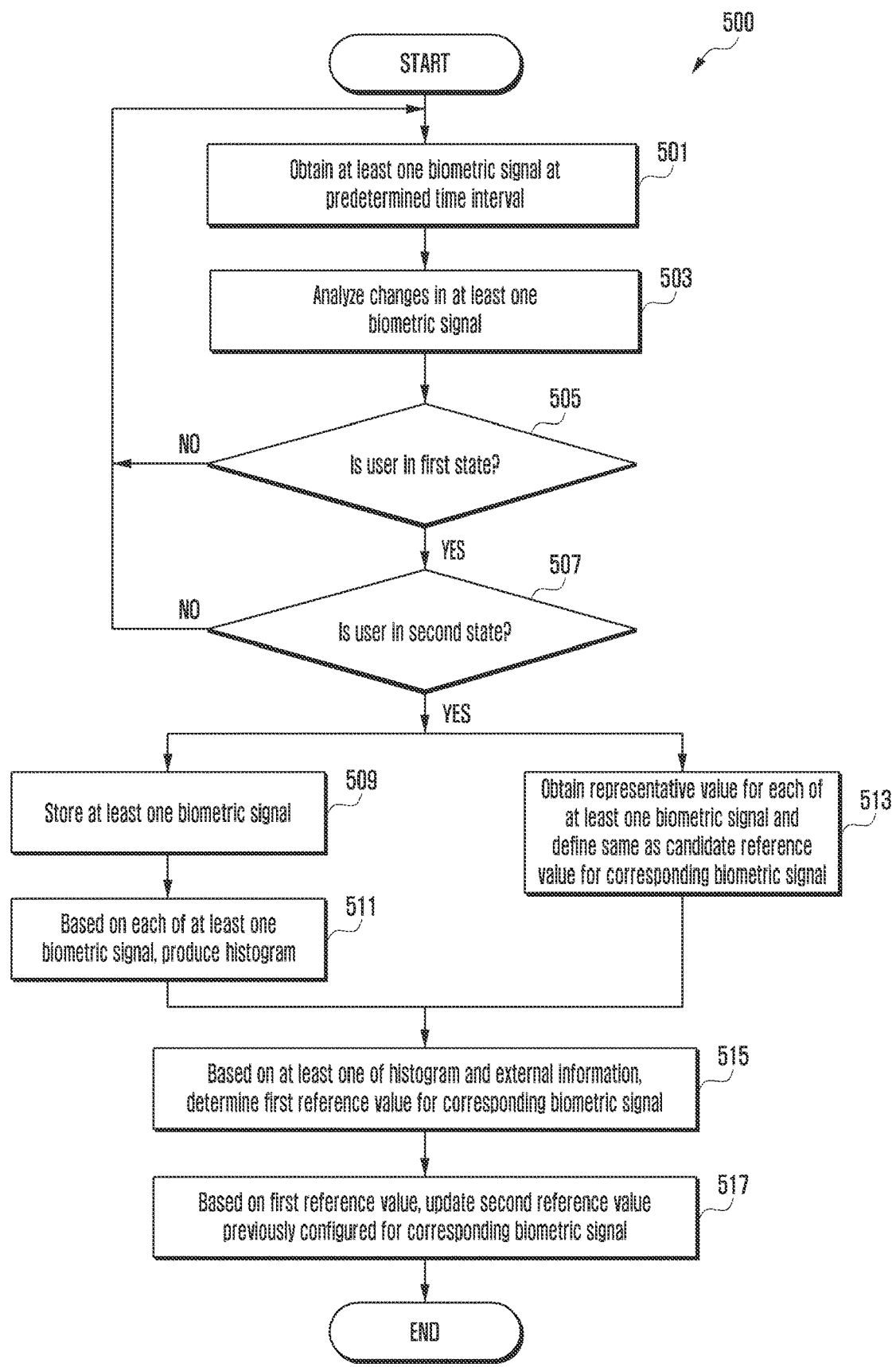
FIG. 5 is a flowchart explaining a method for determining a reference value for providing personalized biometric information based on a biometric signal according to various embodiments of the disclosure.

FIG. 5 is a flowchart 500 explaining a method for determining a reference value for providing personalized biometric information based on a biometric signal according to various embodiments of the disclosure.

In an embodiment, FIG. 5 embodies the respective operations in FIG. 4 described above, and the operations in FIG. 5, which are similar to those in FIG. 4, may refer to the description related to FIG. 4.

Referring to FIG. 5, a processor (e.g., the processor 250 in FIG. 2) may obtain at least one biometric signal through a sensor module (e.g., the sensor module 240 in FIG. 2) at a predetermined time interval in operation 501.

In an embodiment, the sensor module may include a biometric sensor (e.g., a PPG sensor or a skin temperature sensor), an acceleration sensor, and the like.

In an embodiment, the processor may obtain a continuous PPG value, such as a heart rate value, a blood pressure value, or the like, from the biometric sensor (e.g., the PPG sensor). The processor may obtain a continuous skin temperature value from the biometric sensor (e.g., the skin temperature sensor). The processor may obtain a continuous acceleration value for the motion of the electronic device detected by the acceleration sensor.

In an embodiment, the processor may analyze a change in at least one biometric signal in operation 503, and may determine whether or not the user is in a first state in operation 505.

In an embodiment, the first state may include a static state. In an embodiment, the static state may include a static stable state and a static unstable state.

In an embodiment, the static state (e.g., the static stable state) may include the case where a heart rate value or a blood pressure value, which was increased due to the motion of the electronic device, is maintained for a predetermined period of time.

In an embodiment, the static state (e.g., the static unstable state) may include at least one of the case where a biometric signal value obtained from the biometric sensor is increased relative to a predefined biometric signal value in the state in which no motion of the electronic device is detected or the case where the increased state in the biometric signal value is maintained for a predetermined period of time.

In an embodiment, Equation 1 below represents a condition for determining whether or not the user is in a first state (e.g., the static state). Although the following embodiments will be described on the assumption that the biometric signal denotes heart rate (HR), the embodiments are not limited thereto, and the biometric signal may denote blood pressure (BP).

$$\frac{HR(t_i) - HR(t_i - \Delta T)}{\Delta t} > \tau_{HR} \qquad \text{Equation 1}$$

In an embodiment, each interval $T_i$ may be defined as a period of time $\Delta T$ from time $(t_i - \Delta T)$ to time $(t_i)$. In an embodiment, the difference between the end time points of two consecutive intervals may be $(t_{(i+1)} - t_i) = dt > 0$. In an embodiment, when $0 < dt < \Delta T$, the two intervals may overlap each other.

In an embodiment, if the interval during which the heart rate (or blood pressure) increases, the interval during which the increased state of the heart rate (or blood pressure) is maintained for a predetermined period of time, and the interval during which the increased heart rate (or blood pressure) decreases are detected in the state in which no motion of the electronic device is detected, the processor may determine that the user is in a static state (e.g., a static unstable state).

For example, if the heart rate in the interval $T_i$ satisfies Equation 1 (for example, if the incremental slope of the biometric signal exceeds a specific value $\tau_{HR}$), the processor may determine the interval $T_i$ as an "increasing interval", and may determine that the user is in a static state (e.g., a static unstable state).

In an embodiment, for example, if $T_0$ is determined as an increasing point, and if the difference between a representative value of the biometric signal for all intervals $T_i$ (i=1, 2, ..., L) from $T_1$ to the current interval $T_L$ and a representative value for the interval $T_{-1}$ before entering the increasing point exceeds a predetermined value, the processor may determine the intervals $T_1$ to $T_L$ to be in a static state (e.g., a static unstable state).

In an embodiment, if the user is in a first state, the processor may determine whether or not the user is in a second state in operation 507.

In an embodiment, the second state may include a stable state.

In an embodiment, the processor may determine whether or not the user is in the second state on the basis of at least one piece of biometric information, such as heart rate, heart rate variation, and blood pressure values.

In an embodiment, if the user is in the second state, the processor may store at least one biometric signal in the memory (e.g., the memory 220 in FIG. 2) in operation 509. For example, the processor may store, in the memory, each piece of biometric information, such as heart rate, heart rate variation, and blood pressure values, in the stable state interval.

In an embodiment, Equations 2 to 5 below may be used as a method for extracting the stable state interval.

In an embodiment, assuming that three-axis acceleration signals are ACCx, ACCy, and ACCz, respectively, $f_{motion}$ may be a feature indicating the magnitude of acceleration ($\|ACC\|$) extracted on the basis of the acceleration signal in the interval. The $f_{motion}$ may include the magnitude of acceleration ($\|ACC\|$), standard deviation $\sigma$ (ACC), and the like.

In an embodiment, the $f_{motion}$ may be defined as acticount to calculate the degree of motion for each interval. The acticount may be defined as Equation 2 below.

$$Acticount = \sum\nolimits_{\|fACC(t)\| > Acticount_0} \|fACC(t)\| \qquad \text{Equation 2}$$

For example, the processor may obtain a magnitude value of an acceleration signal f ACC filtered by a band-pass filter in order to remove signals other than the motion of the electronic device. The processor may summate the obtained magnitude values of the filtered acceleration signals f ACC, which are equal to or more than a predefined $Acticount_0$, thereby obtaining acticount.

In an embodiment, the processor may extract an interval during which a motion feature (e.g., the acticount) is equal to or less than a predetermined level for a predetermined period of time (e.g., n minutes) immediately before the current interval and during which no biometric signal (e.g., the heart rate) is increased using the obtained degree of motion for each interval.

In an embodiment, in order to determine whether or not the extracted interval corresponds to a stable state, the processor may measure a range of changes in the biometric signals, such as heart rate, blood pressure, skin temperature, and the like, in the extracted interval.

In an embodiment, the processor may determine, as a stable state, the interval during which the range of changes of the biometric signals does not exceed a predetermined range and is maintained for a predetermined period of time.

In an embodiment, assuming that $\Delta t$ is the minimum time unit for dividing each interval, all intervals (e.g., $T_x$) may be defined as I small intervals having a period of time $\Delta t$.

The embodiment will be described on the assumption that, for example, the average value of the biometric signal (e.g., the heart rate) for the current interval $T_L = (t_L - \Delta T \sim t_L)$ is $\overline{HR_L}$. As a result of calculation using Equations 3 and 4 below, if an interval in which the difference in the biometric signal (e.g., the heart rate) between all consecutive minimum time ($\Delta t$) units in the interval and the standard deviation thereof are equal to or less than predetermined values ($r_{HR1}$ and $r_{HR2}$) is detected, the processor may determine the interval satisfying the condition of the predetermined values ($r_{HR1}$ and $r_{HR2}$) to be a stable state interval.

$$HR(t_L(i)(\Delta t)) - HR(t_L - (i+1)(\Delta t)) < r_{HR1}, (i = 0, \ldots, I-1) \quad \text{Equation 3}$$

$$\sqrt{\frac{\sum_{i=0 \sim I-1}(HR(t_L - i\Delta t) - \overline{HR})^2}{I}} < r_{HR2} \quad \text{Equation 4}$$

In an embodiment, the processor may produce a histogram on the basis of each of the at least one biometric signal in operation 511. For example, the processor may produce a histogram for each of the at least one biometric signal on the basis of each of the at least one biometric signal for a second state (e.g., a stable state) of the user.

In an embodiment, the histogram for each of the at least one biometric signal may be the accumulated data on each of the at least one biometric signal, which have recently been obtained for a predetermined period of time (e.g., 10 days).

In an embodiment, if the user is in a second state (e.g., a stable state), the processor may obtain representative value for the respective of the at least one biometric signal, and may define the representative value as candidate biometric signal reference value for the of the at least one respective biometric signal in operation 513, independently from operation 509 and operation 511 described above.

In an embodiment, Equation 5 below is intended to extract a representative value for each biometric signal in the interval that is determined as the second state (e.g., the stable state). In an embodiment, the function f{x} for extracting a representative value for each biometric signal in the interval determined as the second state (e.g., the stable state) may be specified as one of an average value, a mode value, and a median value. The processor may multiply the result of a representative value function f{x} by a constant (e.g., $C_1$), and may add another constant (e.g., $C_2$) thereto, thereby obtaining a candidate reference value B* for the biometric signal (e.g., the heart rate).

$$B_i^* = C_1 f\{HR(T)\} + C_2 \quad \text{Equation 5}$$

In an embodiment, the processor may determine the candidate biometric signal reference value as a first reference value for the corresponding biometric signal on the basis of at least one of the histogram or external information in operation 515.

For example, if the candidate reference value for the biometric signal (e.g., the heart rate) is included within the specific range of the histogram produced in operation 511, the processor may determine the candidate biometric reference value as a first reference value for the corresponding biometric signal (e.g., the heart rate).

In an embodiment, the processor may use Equations 6 and 7 below in order to reduce an error when determining the candidate reference value for the biometric signal (e.g., a candidate reference value for the heart rate) as a first reference value for the corresponding biometric signal.

In an embodiment, if the obtained candidate reference value (e.g., B*) for the corresponding biometric signal (e.g., the heart rate) is included within a reference range of the entire data histogram (e.g., H) (e.g., a bin of upper 80% of the histogram) for each biometric signal of the user for a predetermined period of time (e.g., last 72 hours), and if the obtained candidate reference value (e.g., B*) is included within the range equal to or more than a reference percentage (e.g., $\rho_2$) based on the representative value (e.g., $\overline{H}$) (e.g., a mode value, a median value, or an average value) of the histogram (e.g., the range within 80% of the average value of the histogram), the processor may determine the candidate reference value (e.g., B*) for the biometric signal (e.g., the heart rate) as a first reference value for the biometric signal (e.g., the heart rate).

$$\frac{\sum_{i=H(i)>H(B^*)} H(i)}{\sum H} > \rho_1 \quad \text{Equation 6}$$

$$\overline{H} - h \leq B^* \leq \overline{H} + h \text{ when } \frac{\sum_{i=R-h \sim H+h} H(j)}{\sum H} > \rho_2 \quad \text{Equation 7}$$

In an embodiment, if the value of the histogram bin to which the candidate reference value B* for the corresponding biometric signal (e.g., heart rate) is equal to or more than a specific percentage of the total histogram sum, the processor may determine the candidate reference value B* for a biometric signal (e.g., heart rate) as a first reference value for heart rate.

In an embodiment, the first reference value for the biometric signal may be determined on the basis of the external information.

In an embodiment, the external information may include demographic information. For example, the demographic information may include information such as gender, age, climate, race, and the like. For example, the processor may determine a candidate reference value included within a specific range of the demographic information, among the candidate reference values for the biometric signal (e.g., the heart rate), as a first reference value for the corresponding biometric signal (e.g., the heart rate).

In an embodiment, the processor may update a second reference value, which was previously configured for the corresponding biometric signal, on the basis of the determined first reference value in operation 517.

In an embodiment, the processor may apply predetermined weights (e.g., $\omega$ and $(1-\omega)$) to the reference value B* (e.g., the first reference value) of the corresponding biometric signal and the reference value B (e.g., the second reference value), which was previously configured for the corresponding biometric signal, as shown in Equation 8 below. The processor may update the previously configured second reference value with the reference value B obtained by applying the weight thereto.

$$B = \omega B + (1 - \omega)B^* \quad \text{Equation 8}$$

In an embodiment, Equations 1 to 8 are provided to facilitate the description of the respective operations and are intended for determining the activity state of the user, obtaining a candidate reference value for the biometric signal, determining a reference value for the biometric signal, and updating the reference value for the biometric signal, but equations are not limited to Equations 1 to 8 described above.

Figure 6:
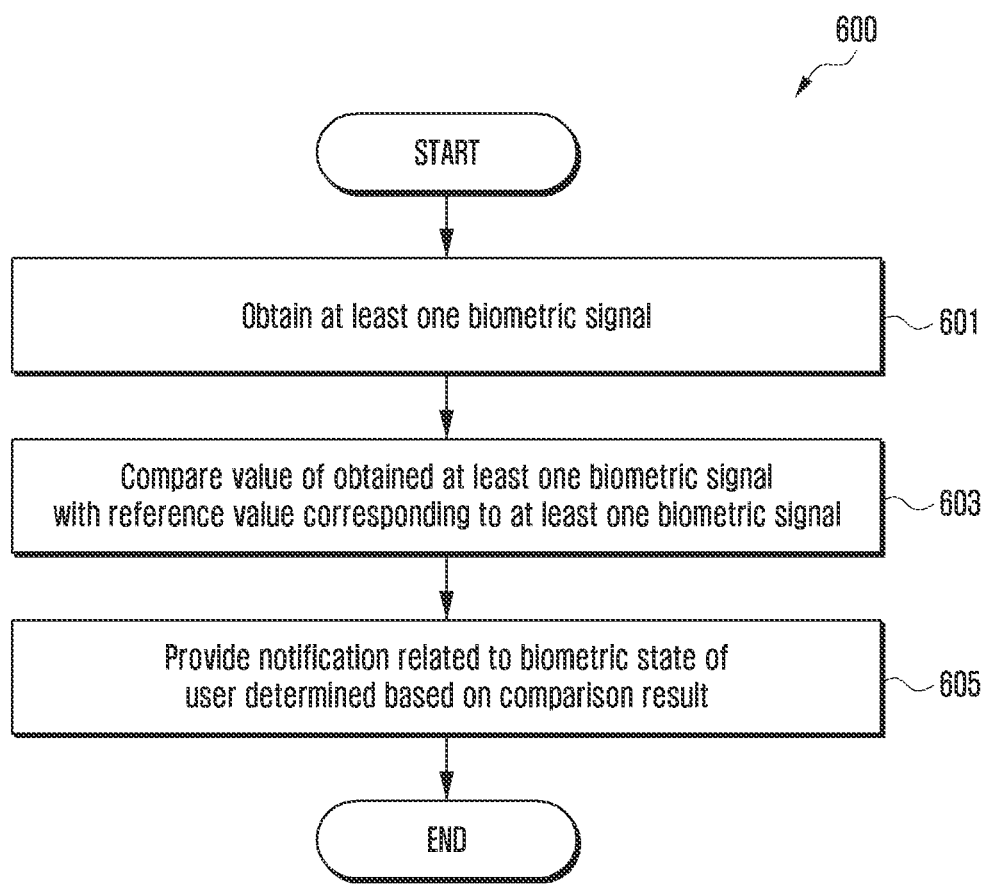
FIG. 6 is a flowchart explaining a method for providing personalized biometric information based on a biometric signal according to various embodiments of the disclosure.

FIG. 6 is a flowchart 600 explaining a method for providing personalized biometric information based on a biometric signal according to various embodiments of the disclosure.

Referring to FIG. 6, a processor (e.g., the processor 250 in FIG. 2) may obtain at least one biometric signal through a sensor module (e.g., the sensor module 240 in FIG. 2) in operation 601.

In an embodiment, the processor may compare value of the obtained at least one biometric signal with reference value corresponding to the at least one biometric signal (e.g., the reference value B obtained using Equation 8) in operation 603.

In an embodiment, the processor may provide a notification of personalized information related to the biometric state of the user determined on the basis of the comparison result in operation 605.

In an embodiment, the personalized information related to the biometric state of the user may include health information, stress information, BP information, and the like. In an embodiment, the personalized information related to the biometric state of the user may be provided in the form of at least one of a message, a pop-up window, or a sound. For example, the personalized information related to the biometric state of the user may include the content such as "Personalization of user's biometric signals is complete.", "User is in stress level 4. You need a break.", and the like.

In an embodiment, the memory (e.g., the memory 220 in FIG. 2) may store instructions. In an embodiment, the operations related to FIGS. 1 to 6 described above may be performed by a mechanism (e.g., a processor) that can read the instructions stored in the memory.

The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A method of providing biometric information based on a biometric signal, the method comprising:
   identifying a state of an electronic device based on a motion signal obtained from an acceleration sensor of the electronic device;
   obtaining, via a photoplethysmography (PPG) sensor of the electronic device, at least one first heart rate value and at least one first heart rate variation value for a predetermined period of time when the identified state of the electronic device is in static state;
   updating a heart rate reference value based on the at least one first heart rate value and a heart rate variation reference value based on the at least one first heart rate variation value; and
   obtaining, via the PPG sensor, a second heart rate value and a second heart rate variation value,
   wherein the obtained second heart rate value and second heart rate variation value are used to be compared with the updated heart rate reference value and the updated heart rate variation reference value respectively for determining biometric information,
   wherein the biometric information is provided based on demographic information, the demographic information including at least one of a gender, an age, or a race, and
   wherein the biometric information is included within a specific range of the demographic information corresponding to demographic information of a user wearing the electronic device.

2. The method of claim 1, further comprising:
   identifying, in case that the motion signal is less than a threshold value, the state of the electronic device to be the static state.

3. The method of claim 1, further comprising:
   storing, in a memory of the electronic device, the obtained at least one first heart rate value and the obtained at least one first heart rate variation value.

4. The method of claim 1, further comprising:
   storing, in a memory of the electronic device, the updated heart rate reference value and the updated heart rate variation reference value.

5. The method of claim 1, further comprising:
   transmitting, via wireless communication circuitry of the electronic device, to an external electronic device, the at least one first heart rate value and the at least one first heart rate variation value,
   wherein the wireless communication circuitry includes Bluetooth communication circuitry.

6. The method of claim 1, wherein the electronic device is a wearable electronic device.

7. An electronic device comprising:
   wireless communication circuitry;
   an acceleration sensor;
   a photoplethysmography (PPG) sensor;
   memory storing one or more computer programs; and
   one or more processors communicatively coupled to the wireless communication circuitry, the acceleration sensor, the PPG sensor, and the memory,
   wherein the one or more computer programs include computer-executable instructions that, when executed by the one or more processors individually or collectively, cause the electronic device to:
   identify a state of the electronic device based on a motion signal obtained from the acceleration sensor;
   obtain, via the PPG sensor, at least one first heart rate value and at least one first heart rate variation value for a predetermined period of time when the identified state of the electronic device is in static state;
   update a heart rate reference value based on the at least one first heart rate value and a heart rate variation reference value based on the at least one first heart rate variation value; and
   obtain, via the PPG sensor, a second heart rate value and a second heart rate variation value,
   wherein the obtained second heart rate value and second heart rate variation value are used to be compared with the updated heart rate reference value and the updated heart rate variation reference value respectively for determining biometric information,
   wherein the biometric information is provided based on demographic information, the demographic information including at least one of a gender, an age, or a race, and
   wherein the biometric information is included within a specific range of the demographic information corresponding to demographic information of a user wearing the electronic device.

8. The electronic device of claim 7, wherein the one or more computer programs further include computer-executable instructions that, when executed by the one or more processors individually or collectively, cause the electronic device to:
   identify, in case that the motion signal is less than a threshold value, the state of the electronic device to be the static state.

9. The electronic device of claim 7, wherein the one or more computer programs further include computer-executable instructions that, when executed by the one or more processors individually or collectively, cause the electronic device to:
   store, in the memory, the obtained at least one first heart rate value and the obtained at least one first heart rate variation value.

10. The electronic device of claim 7, wherein the one or more computer programs further include computer-executable instructions that, when executed by the one or more processors individually or collectively, cause the electronic device to:
    store, in the memory, the updated heart rate reference value and the updated heart rate variation reference value.

11. The electronic device of claim 7, further comprising:
    wireless communication circuitry, wherein the one or more computer programs further include computer-executable instructions that, when executed by the one or more processors individually or collectively, cause the electronic device to:
transmit, via the wireless communication circuitry, to an external electronic device, the at least one first heart rate value and the at least one first heart rate variation value, and
wherein the wireless communication circuitry includes Bluetooth communication circuitry.

12. The electronic device of claim 7, wherein the electronic device is a wearable electronic device.

13. One or more non-transitory computer-readable storage media storing one or more computer programs including computer-executable instructions that, when executed by one or more processors of an electronic device individually or collectively, cause the electronic device to perform operations, the operations comprising:
identifying a state of an electronic device based on a motion signal obtained from an acceleration sensor of the electronic device;
obtaining, via a photoplethysmography (PPG) sensor of the electronic device, at least one first heart rate value and at least one first heart rate variation value for a predetermined period of time when the identified state of the electronic device is in static state;
updating a heart rate reference value based on the at least one first heart rate value and a heart rate variation reference value based on the at least one first heart rate variation value; and
obtaining, via the PPG sensor, a second heart rate value and a second heart rate variation value,
wherein the obtained second heart rate value and second heart rate variation value are used to be compared with the updated heart rate reference value and the updated heart rate variation reference value respectively for determining biometric information,
wherein the biometric information is provided based on demographic information, the demographic information including at least one of a gender, an age, or a race, and
wherein the biometric information is included within a specific range of the demographic information corresponding to demographic information of a user wearing the electronic device.

14. The one or more non-transitory computer-readable storage media of claim 13, the operations further comprising:
identifying, in case that the motion signal is less than a threshold value, the state of the electronic device to be the static state.

15. The one or more non-transitory computer-readable storage media of claim 13, the operations further comprising:
storing, in a memory of the electronic device, the obtained at least one first heart rate value and the obtained at least one first heart rate variation value.

16. The one or more non-transitory computer-readable storage media of claim 13, the operations further comprising:
storing, in a memory of the electronic device, the updated heart rate reference value and the updated heart rate variation reference value.

17. The one or more non-transitory computer-readable storage media of claim 13, the operations further comprising:
transmitting, via wireless communication circuitry of the electronic device, to an external electronic device, the at least one first heart rate value and the at least one first heart rate variation value,
wherein the wireless communication circuitry includes Bluetooth communication circuitry.

18. The one or more non-transitory computer-readable storage media of claim 13, wherein the electronic device is a wearable electronic device.

* * * * *